US012670977B2

(12) United States Patent  (10) Patent No.:  US 12,670,977 B2
Haidar  (45) Date of Patent:  Jun. 30, 2026

(54) INSULIN DELIVERY SYSTEMS, METHODS, AND DEVICES

(71) Applicant: Ypsomed AG, Burgdorf (CH)

(72) Inventor: Ahmad Mohamad Haidar, Montreal (CA)

(73) Assignee: mylife Diabetes Care AG, Burgdorf (CH)

( * ) Notice: Subject to any disclaimer, the term of this patent is extended or adjusted under 35 U.S.C. 154(b) by 238 days.

(21) Appl. No.: 17/998,209

(22) PCT Filed: May 20, 2021

(86) PCT No.: PCT/US2021/033293

§ 371 (c)(1),
(2) Date: Nov. 8, 2022

(87) PCT Pub. No.: WO2021/236864

PCT Pub. Date: Nov. 25, 2021

(65) Prior Publication Data

US 2023/0238104 A1     Jul. 27, 2023

Related U.S. Application Data

(60) Provisional application No. 63/028,899, filed on May 22, 2020.

(51) Int. Cl.
G16H 20/17     (2018.01)
A61B 5/145     (2006.01)

(52) U.S. Cl.
CPC ......... G16H 20/17 (2018.01); A61B 5/14532 (2013.01)

(58) Field of Classification Search
CPC ........ G16H 20/17; G16H 40/67; G16H 50/20; A61B 5/14532
See application file for complete search history.

(56) References Cited

U.S. PATENT DOCUMENTS

| | | | |
|---|---|---|---|
| 11,878,145 B2 * | 1/2024 | Haidar ................... | G16H 20/17 |
| 2016/0256629 A1 | 9/2016 | Grosman et al. | |
| 2016/0279336 A1 * | 9/2016 | Roy ....................... | G16H 20/17 |
| 2018/0200435 A1 * | 7/2018 | Mazlish ............ | A61M 5/14248 |
| 2018/0289891 A1 * | 10/2018 | Finan .................... | G16H 20/17 |
| 2020/0101222 A1 | 4/2020 | Lintereur et al. | |

FOREIGN PATENT DOCUMENTS

WO     2018/204568     11/2018

OTHER PUBLICATIONS

Schmidt S, Nørgaard K. Bolus calculators. J Diabetes Sci Technol. Sep. 2014 (Year: 2014).*
International Search Report of the International Searching Authority pertaining to International Application No. PCT/US2021/033293; Date of Mailing: Aug. 9, 2021; 5 pages.
Written Opinion of the International Searching Authority pertaining to International Application No. PCT/US2021/033293; Date of Mailing: Aug. 9, 2021; 9 pages.

* cited by examiner

*Primary Examiner* — Eliza A Lam

(74) *Attorney, Agent, or Firm* — Dorsey & Whitney LLP

(57)     ABSTRACT

A system includes a controller that is in communication with a medication delivery device and that includes control logic. The control logic is operative to: calculate a meal bolus; calculate a meal bolus correction that is based, at least in part, on a glucose level and also whether the glucose level is above or below a threshold; and calculate a corrected meal bolus based, at least in part, on the meal bolus and the meal bolus correction.

10 Claims, 4 Drawing Sheets

300

Calculating a meal bolus — 302

Calculating a meal bolus correction that is based, at least in part, on: a glucose level, whether the glucose level is above or below a threshold, and whether an IOB level is positive or negative — 304

Calculating a corrected meal bolus based, at least in part, on the meal bolus and the meal bolus correction — 306

INSULIN DELIVERY SYSTEMS, METHODS, AND DEVICES

This application is a 371 National Phase entry of International Patent Application No. PCT/US2021/033293, filed May 20, 2021, entitled "INSULIN DELIVERY SYSTEMS, METHODS, AND DEVICES," which claims priority to U.S. Provisional Patent Application No. 63/028,899, filed May 22, 2020, entitled "INSULIN DELIVERY SYSTEMS, METHODS, AND DEVICES", each of which is incorporated by reference herein, in the entirety and for all purposes.

FIELD OF THE DISCLOSURE

The present disclosure relates to the control of physiological glucose concentrations. More particularly, the present disclosure relates to closed loop systems and methods for controlling physiological glucose concentrations in a patient.

BACKGROUND

Subcutaneous insulin replacement therapy has proven to be the regimen of choice to control diabetes. Insulin is administered via either multiple daily injections or an infusion pump with dosages being informed by capillary glucose measurements made several times a day by a blood glucose meter. This conventional approach is known to be imperfect as day to day (and in fact moment to moment) variability can be significant. Further, this approach can be burdensome to the patient as it requires repeated finger sticks, a rigorous monitoring of food intake, and vigilant control of insulin delivery.

The advent of glucose measurement devices such as a continuous glucose monitor (CGM) creates the potential to develop a closed loop artificial pancreas (AP) system. An AP system uses glucose data provided by the CGM in a dosing/control algorithm executed on a controller that provides direction to an infusion pump, and the pump administers medication to the patient.

SUMMARY

In Example 1, a system to control glucose in a patient is disclosed. The system includes a controller in communication with a medication delivery device. The controller includes control logic operative to: calculate a meal bolus; calculate a meal bolus correction that is based, at least in part, on a glucose level and also whether the glucose level is above or below a threshold; and calculate a corrected meal bolus based, at least in part, on the meal bolus and the meal bolus correction.

In Example 2, the system of Example 1, wherein the meal bolus correction is based, at least in part, on an insulin-on-board (JOB) level when the glucose level is below the threshold and the IOB level is negative. In Example 2, the meal bolus correction can be calculated by (BG–target)/Si–IOB.

In Example 3, the system of any of the preceding Examples, wherein the meal bolus correction is based, at least in part, on the IOB level when the glucose level is above the threshold and the IOB level is positive. In Example 3, the meal bolus correction can be calculated by (BG–target)/Si–IOB.

In Example 4, the system of any of the preceding Examples, wherein the meal bolus correction does not correct for IOB when the glucose level is above the threshold and the IOB level is negative. In Example 4, the meal bolus correction can be calculated by (BG–target)/Si.

In Example 5, the system of any of the preceding Examples, wherein the meal bolus correction does not correct for IOB when the glucose level is below the threshold and the IOB level is positive. In Example 5, the meal bolus correction can be calculated by (BG–target)/Si.

In Example 6, the system of any of Examples 2-5, wherein IOB is based, at least in part, on mini-bolus corrections.

In Example 7, the system of any of Examples 2-6, wherein IOB is based, at least in part, insulin deliveries over a predetermined period of time prior to calculating the meal bolus correction.

In Example 8, the system of any of Examples 2-7, wherein IOB is calculated by a linear decay model, a curvilinear model, or a two-compartment model.

In Example 9, the system of any of Examples 1-8, wherein the meal bolus correction is based, at least in part, on a difference between the glucose level and a target glucose level.

In Example 10, the system of any of Examples 1-9, wherein the meal bolus correction is based, at least in part, on an insulin sensitivity.

In Example 11, the system of any of Examples 1-10, wherein the meal bolus is based, at least in part, on a meal carbohydrate content and a carbohydrate ratio.

In Example 12, the system of any of Examples 1-11, further comprising the medication delivery device configured to deliver insulin to the patient, in response to the calculated corrected meal bolus.

In Example 13, the system of any of Examples 1-12, further comprising a glucose measurement device in communication with the controller and configured to measure the glucose level.

In Example 14, a method is disclosed. The method includes calculating a meal bolus. The method further includes calculating a meal bolus correction that is based, at least in part, on a glucose level, whether the glucose level is above or below a threshold, and whether an insulin-on-board (IOB) level is positive or negative. The method further includes calculating a corrected meal bolus based, at least in part, on the meal bolus and the meal bolus correction.

In Example 15, the method of Example 14, wherein the meal bolus correction is based, at least in part, on the IOB level when the glucose level is below the threshold and the IOB level is negative.

In Example 16, the method of any of Examples 14 and 15, wherein the meal bolus correction is based, at least in part, on the IOB level when the glucose level is above the threshold and the IOB level is positive.

In Example 17, the method of any of Examples 14-16, wherein the meal bolus correction does not correct for IOB when the glucose level is above the threshold and the IOB level is negative.

In Example 18, the method of any of Examples 14-17, wherein the meal bolus correction does not correct for IOB when the glucose level is below the threshold and the IOB level is positive.

In Example 19, the method of any of Examples 14-18, wherein the meal bolus correction is based, at least in part, on insulin sensitivity and a difference between the glucose level and a target glucose level.

In Example 20, a non-transitory computer-readable medium is disclosed as including instructions that cause a hardware processor to: calculate a meal bolus; calculate a meal bolus correction that is based, at least in part, on (1) a glucose level, (2) whether the glucose level is above or below a threshold, and (3) whether an insulin-on-board (IOB) level is positive or negative; and calculate a corrected meal bolus based, at least in part, on the meal bolus and the meal bolus correction.

In Example 21, a non-transitory computer-readable medium is disclosed. The non-transitory computer-readable medium includes instructions that, when executed, cause a hardware processor to carry out the steps of the method of Examples 14-19.

Figure 1:
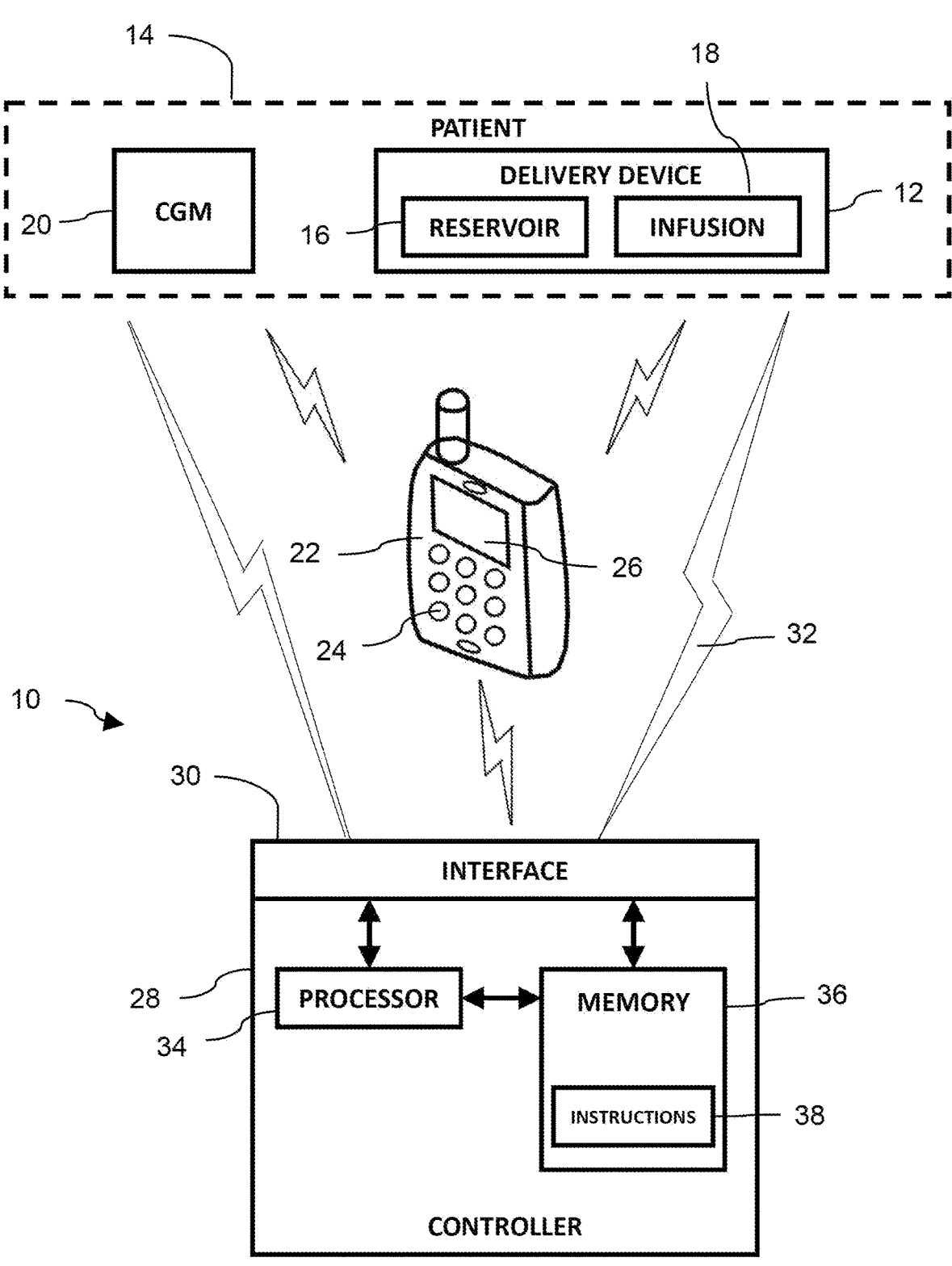
FIG. 1 shows a schematic of a system for controlling physiological glucose, in accordance with certain embodiments of the present disclosure.

While the disclosure is amenable to various modifications and alternative forms, specific embodiments have been shown by way of example in the drawings and are described in detail below. The intention, however, is not to limit the disclosure to the particular embodiments described but instead is intended to cover all modifications, equivalents, and alternatives falling within the scope the appended claims.

DETAILED DESCRIPTION

Closed loop insulin delivery systems automatically adjust insulin delivery in response to measured glucose levels. As will be described in more detail below, these systems automatically adjust a basal insulin delivery rate at regular intervals, such as every 5 to 15 minutes, and calculate meal boluses based, at least in part, on information such as meal carbohydrate content and pre-meal glucose levels. When calculating meal boluses, if a patient's glucose levels are low, the systems are designed to apply negative corrections to reduce the size of the meal boluses. However, the systems are also designed to reduce the basal insulin delivery rate before meals if a patient's glucose levels are low. As a result, in certain circumstances, the systems apply multiple negative corrections, which may increase the likelihood of post-prandial hyperglycemia. Certain embodiments of the present disclosure are accordingly directed to systems, methods, and devices for calculating medication boluses in a closed loop system.

System Hardware

FIG. 1 depicts an exemplary representational block diagram of a system 10 for controlling physiological glucose. The system 10 includes a medication delivery device 12 such as an infusion pump which is removably coupled to a patient 14. The medication delivery device 12 includes at least one medication reservoir 16 which contains a medication. In one embodiment, the medication or drug includes an insulin, such as a regular insulin, an insulin analog such as insulin lispro and insulin glargine, and an insulin derivative, for example. The medication delivery device 12 may deliver at least one medication (e.g., insulin) to a patient 14 via an infusion set 18, which providing a fluid path from the medication delivery device 12 to the patient 14. The infusion set 18 may, for example, provide a fluid path from the medication delivery device 12 to a subcutaneous destination within the patient 14. The medication delivery device 12 or infusion set 18 may include a needle or cannula for inserting into the subcutaneous tissue of the patient. The reservoir 16 can be coupled to a separate pumping device (e.g., plunger, actuator, motor) that assists with pumping medication from the reservoir to the patient.

The system 10 also includes an analyte sensor such as a glucose measurement device 20. The glucose measurement device 20 may be a standalone device or may be an ambulatory device. One example of a glucose measurement device is a continuous glucose monitor (CGM). In specific embodiments, the glucose measurement device 20 may be a glucose sensor such as a Dexcom G6 series continuous glucose monitor, although any suitable continuous glucose monitor may be used. The glucose measurement device 20 is illustratively worn by the patient 14 and includes one or more sensors in communication with or monitoring a physiological space (e.g., an interstitial or subcutaneous space) within the patient 14 and able to sense an analyte (e.g., glucose) concentration of the patient 14. In some embodiments, the glucose measurement device 20 reports a value that is associated with the concentration of glucose in the interstitial fluid, e.g., interstitial glucose (IG). The glucose measurement device 20 may transmit a signal representative of an IG value to the various other components of the system 10.

The system 10 includes a user interface device 22 (hereinafter the "UI 22") that may be used to input user data to the system 10, modify values, and receive information, prompts, data, etc., generated by the system 10. In certain embodiments, the UI 22 is handheld user device programmed specifically for the system 10 or may be implemented via an application or app running on the medication delivery device 12 or a personal smart device such as a phone, tablet, watch, etc. The UI 22 may include input devices 24 (e.g., buttons, switches, icons) and a display 26 that displays a graphical user interface (GUI). The user can interact with the input devices 24 and the display 26 to provide information (e.g., alphanumeric data) to the system 10. In certain embodiments, the input devices 24 are icons (e.g., dynamic icons) on the display 26 (e.g., touchscreen). In one example, a patient uses the UI 22 to announce events such as a meal, start of exercise, end of exercise, emergency stop, etc. In some embodiments, the UI 22 is a graphical user interface (GUI) with a display, where the user interacts with presented information, menus, buttons, etc., to receive information from and provide information to the system 10.

The system 10 also includes a controller 28. Although the controller 28 is shown as being separate from the medication delivery device 12 and the UI 22, the controller 28 can be physically incorporated into either the medication delivery device 12 or the UI 22 or carried out by a remote server. Alternatively, the UI 22 and the medication delivery device 12 may each include a controller 28 and control of the system 10 may be divided between the two controllers 28. Regardless of its physical location within the system 10, the controller 28 is shown as being directly or indirectly communicatively coupled to the medication delivery device 12, the glucose measurement device 20, and the UI 22.

The controller 28 can include or be communicatively coupled to one or more interfaces 30 to communicatively couple via one or more communication links 32 to the medication delivery device 12, the glucose measurement device 20, and/or the UI 22. Example interfaces 30 include wired and wireless signal transmitters and receivers.

Example communication links 32 include a wired communication link (e.g., a serial communication), a wireless communication link such as, for example, a short-range radio link, such as Bluetooth, IEEE 802.11, a proprietary wireless protocol, and/or the like. The term "communication link" may refer to an ability to communicate some type of information in at least one direction between at least two devices. The communication links 32 may be a persistent communication link, an intermittent communication link, an ad-hoc communication link, and/or the like. Information (e.g., pump data, glucose data, drug delivery data, user data) may be transmitted via the communication links 32. The medication delivery device 12, the glucose measurement device 20, and/or the UI 22 may also include one or more interfaces to communicatively couple via one or more communication links 32 to the other devices in the system 10.

The controller 28 can include at least one processor 34 (e.g., a microprocessor) that executes software and/or firmware stored in memory 36 of the controller 28 and that is communicatively coupled to the one or more interfaces 30 and to each other. The software/firmware code contains instructions that, when executed by the processor, cause the controller 28 to perform the functions of the control algorithm described herein. The controller 28 may alternatively or additionally include one or more application-specific integrated circuits (ASICs), field-programmable gate arrays (FPGAs), digital signal processors (DSPs), hardwired logic, or combinations thereof. The memory 36 may include computer-readable storage media in the form of volatile and/or nonvolatile memory and may be removable, non-removable, or a combination thereof. In embodiments, the memory 36 stores executable instructions 38 (e.g., computer code, machine-useable instructions, and the like) for causing the processor 34 to implement aspects of embodiments of system components discussed herein and/or to perform aspects of embodiments of methods and procedures discussed herein, including the control logic described in more detail below. The interfaces 30, the processor 34, and the memory 36 may be communicatively coupled by one or more busses. The memory 36 of the controller 28 is any suitable computer readable medium that is accessible by the processor. Memory may be a single storage device or multiple storage devices, may be located internally or externally to the controller 28, and may include both volatile and non-volatile media. Exemplary memory includes random-access memory (RAM), read-only memory (ROM), electrically erasable programmable ROM (EEPROM), flash memory, CD-ROM, Digital Versatile Disk (DVD) or other optical disk storage, a magnetic storage device, or any other suitable medium which is configured to store data and which is accessible by the controller 28.

The controller 28 may receive information from a plurality of components of the system 10 and feed the information (e.g., pump data, glucose data, drug delivery data, user data) into a control algorithm (as described in more detail below) which determines at least one drug delivery control parameter which may in part govern operation of the medication delivery device 12. In some specific embodiments, the controller 28 may receive pump data from the medication delivery device 12, glucose data from the glucose measurement device 20, and user data from the UI 22. The pump data received may include drug delivery data corresponding to drug dosages delivered to the patient 14 by the medication delivery device 12. The pump data may be supplied by the medication delivery device 12 as doses are delivered or on a predetermined schedule. The glucose data received by the controller 28 may include glucose concentration data from the glucose measurement device 20. The glucose data may be supplied at a continuous rate, occasionally or at predefined intervals (e.g., every 5 or 10 minutes).

The pump data, glucose data, drug delivery data, and user data may be provided to the controller 28 as acquired, on a predefined schedule or queued in the memory 36 and supplied to the controller 28 when requested. The user data may be input to the UI 22 in response to user/patient prompts generated by the UI 22 and/or declared by the patient 14 as instructed during training. In some embodiments, at least some of the pump data, glucose data, and/or user data may be retrieved from the memory 36 associated with the controller 28, and some of this data may be retrieved from a memory in the medication delivery device 12. In some embodiments, user interaction with the UI 22 may be minimal with the patient 14 being prompted to start execution of the algorithm implemented by the controller 28 and provide meal and/or exercise announcements. In other embodiments, the user may be prompted to provide various additional data in order to initialize the algorithm implemented by the controller 28.

The at least one drug delivery parameter determined by the controller 28 may be a medication dose or doses, which may at least in part govern drug administration to the patient 14 via the medication delivery device 12. For insulin delivery (e.g., delivery of a rapid acting insulin or ultra-rapid acting insulin), the drug delivery parameter may be a basal rate (e.g., a basal profile including predefined time-varying insulin flow rates over the course of 24 hours), micro-bolus doses (e.g., corrected doses with respect to the basal rate), and/or a meal bolus. The basal delivery is the continuous delivery of insulin at the basal rate needed by the patient to maintain the glucose level in the patient's blood at the desired level outside of post-meal periods. The medication delivery device 12 may provide the basal delivery in basal doses followed by periods of zero flow that average out to the basal rate. In one example, the medication delivery device 12 supplies a basal dose at a fixed interval, and the basal dose is equal to the desired basal rate times the duration of the interval. Occasionally, the user may require a larger amount of insulin due to a change in activity such as eating a meal or other activities that affect the user's metabolism. This larger amount of insulin is herein referred to as a bolus. A meal bolus is a specific amount of insulin that is generally supplied over a short period of time. The nature of the medication delivery device 12 may require delivering the bolus as a continuous flow of insulin for a period or as a series of smaller, discrete insulin volumes supplied over a period. The meal bolus facilitates maintenance of the glucose level as the digestive system supplies a large amount of glucose to the blood stream.

In one embodiment, the drug delivery parameter provided to the medication delivery device 12 is a control signal requesting the pump to deliver a specific amount or volume of medication. In one embodiment, the drug delivery parameter is an analogue or digital signal that the medication delivery device 12 converts to an amount or volume of medication or a number of pump strokes. In some embodiments, the drug delivery parameter is a deviation from the basal insulin dose or current value of the basal insulin profile. The deviation may be an amount or volume of insulin or a percentage of the basal insulin dose. Thus, the system 10 may operate in a closed-loop setting requiring minimal or no interaction from the patient 14 after initial start-up to effect glycemic control.

The term physiological glucose herein refers to the measured concentration of glucose in the body. In some embodiments, physiological glucose may be the concentration of glucose in the blood, which may also be referred to as blood glucose. In other embodiments, physiological glucose may be the concentration of the glucose in the blood plasma, which may be referred to as plasma glucose. The measured value of plasma glucose is typically 10 to 12% higher than blood glucose because the blood cells of the blood have been removed in the plasma glucose determination. The relationship between plasma glucose and blood glucose depends on the hematocrit and can vary from patient to patient and over time. The physiological glucose, abbreviated herein as PG, may be measured indirectly by measuring the glucose concentration in the interstitial fluid which is referred to as interstitial glucose and abbreviated IG.

MMPC Algorithm

Figure 2:
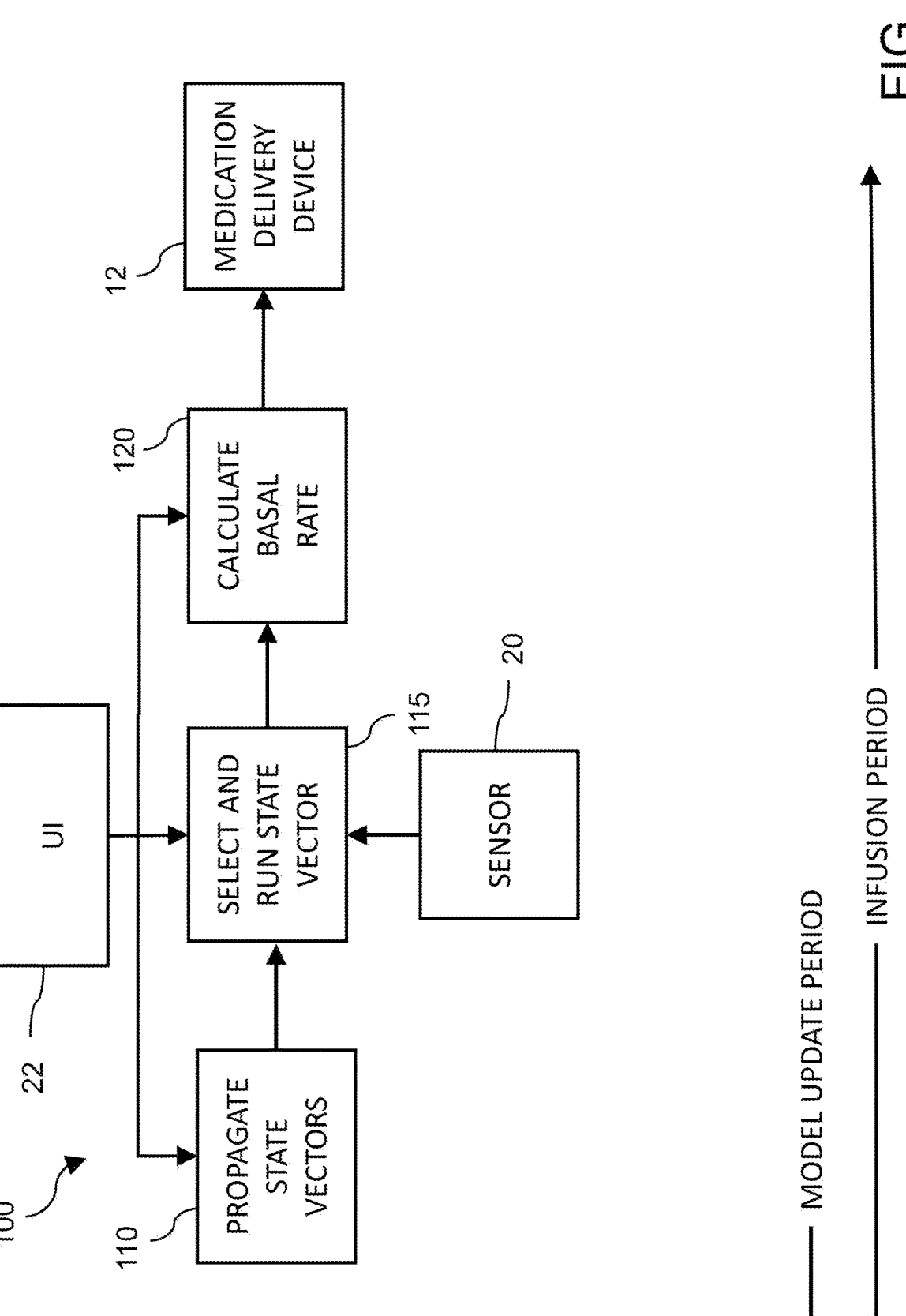
FIG. 2 shows a block diagram of an exemplary model predictive control algorithm, in accordance with certain embodiments of the present disclosure.

In certain embodiments, the controller 28 has control logic in the form of a multi-model predictive controller (MMPC) 100, which is outlined in FIG. 2 and which executes an artificial pancreas algorithm. In other embodiments, the controller 28 has control logic in the form of a proportional-integral-derivative (PID) controller or other types of closed-loop control approaches. Although the description below uses the MMPC 100, other approaches such as PID controllers can be used in connection with the claimed invention.

The MMPC 100 receives glucose concentration data from the glucose measurement device 20 and user data from the UI 22 and determines the amount of medication for the medication delivery device 12 to deliver to the patient 14. The medication delivery device 12 then delivers the requested insulin dose to the patient via the infusion set 18.

The MMPC 100 combines multiple state vectors and their models with a model predictive control algorithm. The MMPC 100 adds improved adaptability to changes in the body and the environment to the controller 28 by propagating multiple state vectors (block 110 in FIG. 2) and selecting the state vector and its model that best matches past data. The selected-state vector and its model are then used by the controller 28 to determine the next basal rate or basal dose of insulin to deliver to the patient in order to achieve the desired physiological glucose level (block 115 in FIG. 2). The use of the multiple state vectors and their models improves the responsiveness of the algorithm to changes in metabolism, digestion, activity or other changes.

In certain embodiments, the MMPC 100 propagates each of the state vectors at each time interval using models, glucose data and covariance matrices with a Kalman filter. In some embodiments, the MMPC 100 retains the previous values of each state vector for a period of time and as each state vector is propagated generating the most current value of each state vector, the oldest value of each state vector is overwritten. Each state vector is associated with a unique model and unique covariance matrices. The MMPC 100 selects a best state vector and its model based on how well the state variable for IG matches the measured values of IG over a period in the past. The MMPC 100 then uses in the selected-state vector and its model in a model-predictive controller where the MMPC 100 propagates the selected-state vector out to a prediction horizon generating a predicted set of physiological glucose values over time. The set of predicted glucose values at corresponding time is herein referred to as a predicted trajectory. The MMPC 100 uses the physiological glucose trajectory and an objective function to determine an optimal insulin trajectory.

In some embodiments, the optimal insulin trajectory is a trajectory of deviations from the basal insulin or basal profile, herein referred to as the basal-deviation trajectory. In these embodiments, the amount of insulin delivered to the body is the predefined basal insulin plus the optimal-basal deviation determined from the insulin trajectory. In these embodiments, the model and the objective function consider the response of the body to meals and insulin levels above or below the predefined basal insulin rate.

A preliminary insulin rate, dose or optimal-basal deviation is taken from the value of the insulin trajectory for the first interval. The MMPC 100 may limit this preliminary insulin rate, dose or optimal-basal deviation before passing the rate or dose request to the medication delivery device 12. In the embodiments where the optimal insulin trajectory is the deviation from the basal profile, the dose request is the sum of the limited-basal deviation plus basal profile. The limited insulin rate, limited dose, or limited-basal deviation is then fed back into the multiple state vectors as an insulin input for the determination of the insulin rate or dose at the next interval.

The Models

A model includes a set of linear difference equations executed by control logic that calculate levels of PG and the IG in a patient's body. In some embodiments, the model comprises eight compartments that track the movement and the persistence of insulin, carbohydrates, and glucose within the body. In some embodiments, the model considers external sources of glucose (carbohydrates) and levels of insulin different from the basal profile.

The movement and persistence of insulin, carbohydrates, and glucose may be driven by several model parameters. The calculated PG values may be used to determine the next micro-bolus of insulin and/or a meal bolus that may be delivered to the patient. The calculated IG may be compared to the measured IG. The MMPC algorithm 100 may comprise a large set of state vectors that each have a model with a unique combination of model parameters.

The model parameters may include but are not limited to insulin sensitivity ($S_I$), insulin time constant ($k_I$), the meal action time constant ($k_C$), sensor time constant ($k_{SENSOR}$), insulin to carbohydrate ratio (ICR).

In some embodiments, the insulin sensitivity ($S_I$) is a function of the estimated basal insulin need, $$S_{INS} = S_{PRM} \frac{7}{I_{OL}/60} S_I = S_P * 7/(I_{EBN}/60),$$

where $S_P$ is a model parameter that controls in part, at least, the effect of insulin on physiological glucose. The estimated basal need of insulin ($I_{EBN}$) is a function of the total daily dose (TDD) and total daily basal (TDB). The insulin to carbohydrate ratio (ICR) reflects the amount of insulin required to remove a given amount of glucose from the blood. The insulin to carbohydrate value may vary from meal to meal, i.e., may have a first value for breakfast, a second value for lunch, and a third value for dinner. The model parameters may include input values at the UI 22, programmed values in the algorithm, or stored values in the memory 36 readable by the controller 28, or a combination of these options.

Target Glucose

As described above, the illustrative MMPC algorithm 100 implemented by the controller uses a target physiological glucose value ($PG_{TGT}$) when determining the optimal deviation from the basal profile. The $PG_{TGT}$ is a fixed value in some embodiments. In other embodiments, $PG_{TGT}$ is modified from a nominal or preset value when various conditions are present or various events occur. The target physiological glucose value may be determined based on user data communicated to the system 10 via the UI's inputs. Such adjustments of the target physiological glucose value may, for example, occur in response to the announcement of meals and/or exercise. The adjustments of the target glucose value may be governed at least in part by a target modification formula or may be based off predefined values to be used when the certain circumstances exist. Additionally, a target value adjustment may persist for a period after the condition or event occurs. The adjustment may be a static or fixed adjustment over this period or alter in magnitude (e.g., decrease linearly in magnitude) as the time period elapses.

The glucose target may be used to determine the optimal deviations from the basal profile as described above. The target physiological glucose value may be altered in response to meal and exercise input data. As part of determining the optimal deviation in the basal profile, the nominal target glucose value may be adjusted from its nominal value. An exemplary nominal target glucose value is 5-6 mmol/L, although other suitable values and ranges (e.g., 5-5.5 mmol/L) may be implemented. The target glucose value may be adjusted in some embodiments if the patient 14 has announced exercise and not yet ended exercise while the MMPC algorithm 100 is determining the optimal deviation of the basal profile. In other embodiments, the target glucose value may be modified for exercise if a period of exercise has occurred for a predetermined period within a predefined time of the current time. In some embodiments, meal data may alter the target physiological glucose value if the patient 14 has announced a meal within a predefined period of the determination of the optimal-basal deviation.

An exercise announcement may modify the physiological glucose target value from a preset or nominal value to an exercise target value. In some embodiments, the exercise target value may be at or about 3 mmol/L greater than the preset or nominal target value. In some embodiments, the preset or nominal target value may be at or about 6 mmol/L and the exercise target value may be at or about 9 mmol/L.

A meal announcement or meal data may be input to a formula which increases the target value based on proximity to the meal. The formula may be arranged such that the meal has a greater effect on the target values in close temporal proximity to the meal. As the time from the consumption of the meal increases, the target value may be altered to a lesser degree. After a certain predefined time period has elapsed, the meal input data may no longer have an effect in determining any target value adjustment and a preset or nominal target value may be used. The effect of the meal event on the target physiological glucose value may change (e.g., decrease) in a linear fashion over time.

After accounting for the above-described announcements, the MMPC 100 calculates a basal rate (block 120 in FIG. 2) and transmits that basal rate to the medication delivery device 12.

Meal Bolus

Figure 3:
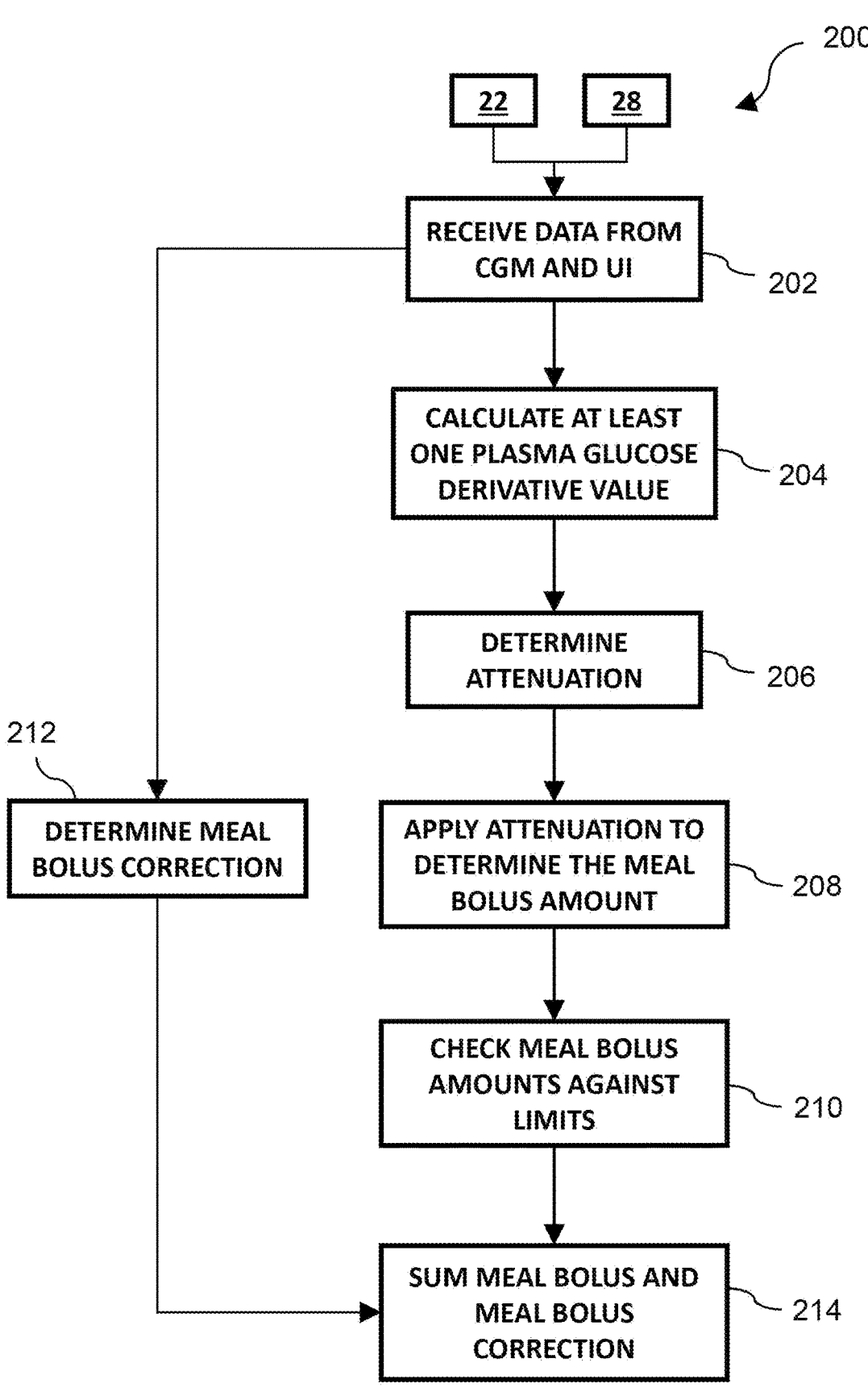
FIG. 3 shows a flowchart detailing various example logic, which may be applied when determining an amount of drug to be delivered in a meal bolus, in accordance with certain embodiments of the present disclosure.

Referring now to the flowchart 200 shown in FIG. 3, various logic rules may be applied when determining an amount of drug (e.g., insulin) to be delivered in a meal bolus to the patient 14 to maintain the physiological glucose concentrations at the desired level or range during and after a meal. In block 202, the current PG concentration is received from the glucose measurement device 20 and the meal data from the UI 22. In block 204, the controller 28 may determine at least the rate of change of the physiological glucose concentration (dPG/dt). The dPG/dt may be determined by any suitable method including the at least one method is described herein. The meal bolus can be determined from the amount of carbohydrates in the meal (CHO), the insulin to carbohydrate ratio (ICR) and a bolus attenuation factor (Palo), where the bolus attenuation factor reduces the meal bolus when the physiological glucose is relatively low and/or decreasing in value. The closed loop control of the physiological glucose provided by the MMPC algorithm 100 can provide a method to provide additional insulin to make up for the reduced meal bolus if needed to maintain euglycemia.

When determining a meal bolus, the system 10 may determine a meal bolus amount with inputs from at least one of the glucose measurement device 20 and the UI 22. A preliminary value for the meal bolus may be the carbohydrate content of the meal divided by an insulin-to-carbohydrate ratio. The preliminary value for the meal bolus may be attenuated based on the physiological glucose values determined by the controller 28. The carbohydrate content of the meal may be explicitly entered at the UI 22 or may be inferred by the controller 28 from meal data supplied at the UI 22. The insulin to carbohydrate ratio may be input at the UI 22 and/or stored in memory 36 that is readable by the controller 28. The carbohydrate content of the meal may be input by the user as a qualitative judgment of the user. For example, the user may indicate a meal size via the UI 22 of the system 10. In some embodiments, the meals size may be selected from a plurality of categories such as, but not limited to: small, medium, large, or snack.

The meal bolus may be calculated from the carbohydrate content of the meal (CHO), the insulin to carbohydrate ratio (ICR), and an attenuation factor. The attenuation factor depends on the physiological glucose concentration and the rate of change of the physiological glucose and determined from a predefined formula in block 206. The meal bolus is determined in block 208.

The meal bolus algorithm may attenuate the meal bolus of small meals differently than larger meals. For example, if the carbohydrate content of the meal is estimated to be above a carbohydrate threshold ($C_{THD}$), then the meal bolus may be calculated as a product of the carbohydrate value (CHO), and the attenuation factor ($A_{CHO}$) divided by the insulin to carbohydrate ratio (ICR):

$$\text{Meal bolus} = \frac{CHO}{ICR} \cdot A_{CHO} \text{ if } CHO > C_{THD}$$

Continuing this example, if the carbohydrate content is estimated to be less than the same carbohydrate threshold, then the meal bolus calculation may be altered to:

$$\text{Meal bolus} = \max\left(0, \frac{CHO - C_{THD} * (1 - A_{CHO})}{ICR}\right) \text{ if } CHO \leq C_{THD}$$

The equation for the meal bolus modifies the reduction of the meal bolus for small meals by the attenuation factor ($A_{CHO}$) so that magnitude of the bolus attenuation for a given $A_{CHO}$ is constant below the carbohydrate threshold. The magnitude of the bolus attenuation proportional to the carbohydrate content of the meal above the carbohydrate threshold and proportional to the carbohydrate threshold for smaller meals below the same carbohydrate threshold. In some embodiments, the carbohydrate threshold is 70 grams, although other suitable thresholds may be provided.

The attenuation factor, $A_{CHO}$, is a function of the physiological glucose and the rate of change of physiological glucose. The attenuation factor increases with both increases in physiological glucose and increasing rates of change of the physiological glucose. The attenuation factor may be bound by a lower value and an upper value. In some embodiments, lower limit of the attenuation factor is 0.8. In some embodiments, the upper limit on the attenuation factor is 1.0. In some embodiments, the attenuation factor can be determined from a spline fit of PG and dPG/dt to the values in Table I.

TABLE I

| attenuation factor values | | | |
| --- | --- | --- | --- |
| | dPG/dt = −3 mmol/L hr | dPG/dt = 0 mmol/L hr | dPG/dt = 3 mmol/L hr |
| PG = 4.0 mmol/L | 0.8 | 0.9 | 0.9 |
| PG = 6.5 mmol/L | 0.8 | 1.0 | 1.0 |
| PG = 9.0 mmol/L | 1.0 | 1.0 | 1.0 |

In some embodiments, the controller 28 may determine the attenuation factor from a set of linear interpolations for physiological glucose (PG) values and rate of change of physiological glucose (dPG/dt) values. The physiological glucose is may be the estimated physiological glucose (PG) determined by the CGM and/or from the selected-state vector. The rate of change of physiological glucose (dPG/dt) may be determined in several fashions. In some embodiments the rate of change of PG is $60*(PG(t)-PG(t-dt))/dt$ where where dt is 20 mins and dPG/dt has units of mmol/L/hr. In the example, the meal attenuation ($A_{CHO}$) ranges from 1.0 to 0.8 with the lower attenuation values resulting when physiological glucose concentration is both low (e.g. below 6.5 mmol/L) and decreasing with time.

Referring now to FIG. 3, the attenuated meal bolus from block 208 may be limited by in block 210 based on the total daily dose of insulin (TDD). In some embodiments, the meal bolus is limited to being equal to or less than a predetermined upper limit. If the meal bolus is greater than the predetermined upper limit, the meal bolus is set equal to the predetermined upper limit. In some embodiments, the upper limit is a fraction of the TDD. In one embodiment, the upper limit is one fifth of TDD. The resulting limited meal bolus from block 210 is then passed to block 214. At block 214, the meal bolus and the meal bolus correction (described in detail immediately below) are combined (e.g., summed) to calculate a corrected meal bolus.

Meal Bolus Correction

As noted above, the system 10 (e.g., via the MMPC 100 as carried out by the controller 28) may reduce the basal rate before meals if the patient's glucose levels are low. As such, when determining whether and to what extent the meal bolus from block 210 should be corrected, the meal bolus correction from block 212 can be calculated to mitigate the risk of correcting too much. For example, the meal bolus correction can be calculated differently in different scenarios depending on conditions of the patient 14.

In certain embodiments, the meal bolus correction calculation is based, at least in part, on the patient's glucose level. The patient's glucose level could be the current PG value or an estimated PG value from the MMPC 100.

In addition to being based on the patient's glucose level itself, the meal bolus correction calculation can be based on whether the patient's glucose level is above or below one or more thresholds. In certain embodiments, the threshold is the patient's target glucose value or the patient's target glucose range (e.g., a range with an upper threshold and a lower threshold). As noted above, the thresholds can be a static threshold or a dynamic threshold in which the threshold is set to account for user announcements such as meal announcements and exercise announcements.

In addition, the meal bolus correction calculation can be based on whether the patient's insulin-on-board (JOB) level is positive or negative, which will be described in more detail below.

In the scenario when the patient's glucose level is above the threshold, the meal bolus correction can be calculated using Equation 1:

$$\text{Meal bolus correction} = (BG-target)/Si-MAX(IOB,0) \qquad \text{Equation 1}$$

where BG=patient's glucose level,
target=patient's target glucose level,
Si=patient's insulin sensitivity,
MAX( )=a maximum operator, and
IOB=patient's insulin-on-board level.

Applying Equation 1, when the patient's glucose level is above the threshold and when the patient's IOB level is positive, the patient's IOB level is used as a negative correction. Put another way, the IOB level is subtracted from the (BG−target)/Si component of Equation 1.

Conversely, when the patient's glucose level is above the threshold but the patient's IOB level is negative, the patient's IOB level is not used as part of the meal bolus correction calculation. This is because the MAX( ) component of Equation 1 will apply a zero (e.g., not permit a negative number) when the IOB level is negative.

In the scenario when the patient's glucose level is below the threshold and the patient's IOB is positive, the meal bolus correction can be calculated using Equation 2:

$$\text{Meal bolus correction} = (BG-target)/Si \qquad \text{Equation 2}$$

Applying Equation 2, when the patient's glucose level is below the threshold and when the patient's IOB level is positive, the patient's IOB level is not used as part of the meal bolus correction calculation. As a result, the meal bolus correction will be a negative number. To show one example, if the patient's insulin sensitivity is calculated as 40 mn/dl per unit, the target glucose level is 100 mg/dl, and the patient's glucose level is 60 mg/dl at meal time, the negative correction would be −1 unit. As such, when the negative meal bolus correction is combined with the uncorrected meal bolus, the resulting corrected meal bolus would be lowered.

In the scenario when the patient's glucose level is below the threshold and the patient's IOB is negative, the meal bolus correction can be calculated using Equation 3:

$$\text{Meal bolus correction} = (BG-target)/Si-IOB \qquad \text{Equation 3}$$

Applying Equation 3, when the patient's glucose level is below the threshold and when the patient's IOB level is negative, the patient's IOB level is used as part of the meal bolus correction calculation.

A negative IOB level may indicate that the patient has experience a suspension of insulin delivery. In applying Equation 3 in the above-described scenario, in certain embodiments, Equation 3 may be capped at zero such that a negative IOB level cannot cause Equation 3 to apply a positive correction to the uncorrected meal bolus. A large negative IOB level may be a result of a prolonged suspension of insulin delivery.

However, depending on characteristics of the suspension (e.g., length, cause of suspension), Equation 3 may not be capped at zero such that a positive meal bolus correction is calculated and applied. A positive meal bolus correction would cause more insulin to be delivered in the case of a prolonged suspension.

In certain embodiments, the IOB levels mentioned above in Equations 1 and 3 are based, at least in part, on previous insulin deliveries. For example, insulin deliveries that have been delivered over a predetermined period of time (e.g., 3 hours, 4 hours) prior to calculating the meal bolus correction can be used to calculate a current estimated IOB level of a patient. In addition, the IOB levels can take into account any mini-bolus deliveries made during that period of time. As mentioned above, mini-boluses can be calculated by the MMPC 100 to make small corrective insulin deliveries. These mini-boluses can be considered positive corrections when the MMPC 100 causes a larger dose to be delivered compared to the programmed basal rate and can be considered negative when the MMPC 100 causes a smaller dose to be delivered compared to the programmed basal rate.

The various basal rate, boluses, and mini-boluses over the period of time can be used as inputs to different methods of calculating the patient's current estimated IOB level. In some embodiments, the basal rate, boluses, and mini-boluses are simply summed together to calculate the current estimated IOB level. In some embodiments, the basal rate, boluses, and mini-boluses are given different weights based on the time of the given delivery and then summed together to calculate the current estimated IOB level. For example, the current estimated IOB level can be calculated using a linear decay model, a curvilinear model, or a two-compartment model.

As noted above, Equations 1-3 use a patient's insulin sensitivity to calculate the meal bolus corrections. Insulin sensitivity is a component that estimates how a patient reacts to insulin deliveries. A high insulin sensitivity indicates that the patient's glucose levels will change more for a given insulin dose amount compared to a patient with a lower insulin sensitivity. Insulin sensitivity is typically expressed in terms of mg/dl per unit of insulin. In certain embodiments, insulin sensitivity can be estimated or based, at least in part, on a patient's total daily dose (TDD).

To summarize, Equation 1 can be used to calculate the meal bolus correction in two scenarios: (1) when a patient's glucose level is higher than a threshold and the patient's IOB level is positive and (2) when a patient's glucose level is higher than a threshold and the patient's IOB level is negative. Equation 2 can be used in the scenario when a patient's glucose level is lower than a threshold and the patient's IOB level is positive. Equation 3 can be used in the scenario when a patient's glucose level is lower than a threshold and the patient's IOB level is negative. Further limits can be placed on Equation 3 such as not permitting a negative IOB level to cause a positive correction.

Referring back to FIG. 3, at block 214, the meal bolus and the meal bolus correction are combined (e.g., summed) to calculate the corrected meal bolus. The calculated corrected meal bolus is then communicated to the medication delivery device 12, which delivers a bolus to the patient 14 in the amount of the calculated corrected meal bolus.

Figure 4:
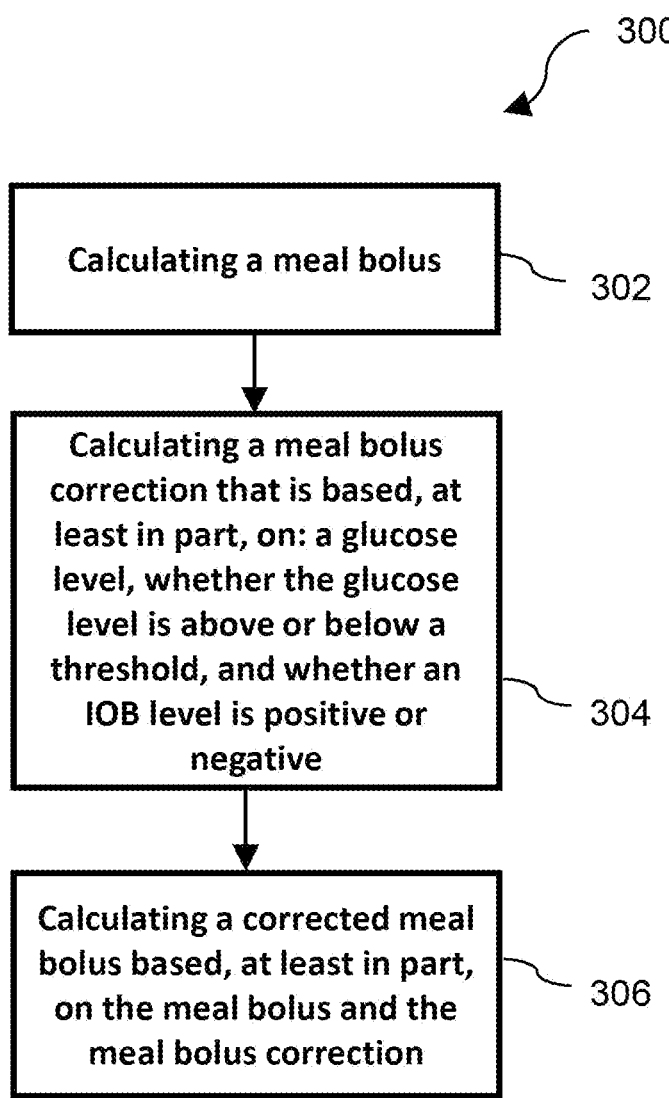
FIG. 4 shows a block diagram of a method, in accordance with certain embodiments of the present disclosure.

FIG. 4 shows a flowchart of a method 300 that can be carried out with the system 10 to calculate a corrected meal bolus. The method 300 includes calculating a meal bolus (e.g., an uncorrected meal bolus) (block 302 in FIG. 4). The method 300 also includes calculating a meal bolus correction that is based, at least in part, on: a glucose level, whether the glucose level is above or below a threshold, and whether an IOB level is positive or negative (block 304 in FIG. 4). The method 300 further includes calculating a corrected meal bolus based, at least in part, on the meal bolus and the meal bolus correction (block 306 in FIG. 4).

Automatic Boluses

To ensure patient safety, the system 10 (e.g., via the MMPC 100 as carried out by the controller 28) can implement various safety rules that limit insulin delivery based on the accumulation of previous insulin deliveries (e.g., estimated IOB or IOB-like levels). However, sometimes these safety rules may prevent the MMPC 100 from correcting high glucose levels. The description below provides approaches for delivering automatic insulin boluses as a "off-ramp" to certain safety guardrails of the MMPC 100. These automatic boluses are separate from and in addition to the basal rate and micro-boluses described above. The automatic boluses can help normalize hyperglycemia without increasing the risk of hypoglycemia.

In certain embodiments, an insulin bolus is triggered or initiated if the amount of insulin needed to normalize a patient's glucose level crosses a threshold. In certain embodiments, the amount of insulin needed is a model-predicted amount of insulin. In one specific example, the amount of insulin needed to normalize glucose levels, designated as a, is calculated as follows:

$$\alpha = (\text{Carb\_on\_board} \times \text{Carb\_sensitivity}) - \text{BOB} + (G - \text{Target\_}G) \times \text{Si} - \text{Control\_IOB}$$

where Carb_on_board=a predicted amount of meal carbohydrate that is ingested but not yet fully absorbed in the body;

Carb_sensitivity=an amount of insulin needed to cover 1 gram of carbohydrate;

BOB=a predicted amount of insulin bolus that is delivered but not yet fully absorbed in the body (e.g., bolus on board);

G=a current estimated glucose level;

Target_G=the target glucose level; and

Control_IOB=a predicted amount of control insulin above the basal rate that is delivered but not yet fully absorbed in the body.

The threshold can be based on a variety of different types of information. For example, the threshold can take into account a patient's total daily insulin dose, body weight, and/or previous glucose levels, among others. If amount of insulin needed to normalize glucose levels crosses the threshold (e.g., is above the threshold) and remains for a certain amount of time, then an insulin bolus is delivered automatically to the patient 14. In certain embodiments, the insulin bolus will be equal amount of insulin needed to normalize glucose levels. In certain embodiments, the insulin bolus will be a fraction of the amount of insulin needed to normalize glucose levels.

As such, the controller 28 can include control logic that is operative to calculated and cause delivery of automatic boluses. The control logic is operative to calculate an amount of insulin needed to normalize glucose levels. The amount of insulin needed to normalize glucose levels can be based, at least in part, on one or more of the following: a predicted amount of meal carbohydrate that is ingested but not yet fully absorbed in the body, an amount of insulin needed to cover 1 gram of carbohydrate, a predicted amount of insulin bolus that is delivered but not yet fully absorbed in the body (e.g., bolus on board), a current estimated glucose level, a target glucose level, and a predicted amount of control insulin above the basal rate that is delivered but not yet fully absorbed in the body. The control logic is further operative to compare the amount of insulin needed to normalize glucose levels to a threshold and determine that the threshold has been crossed (either momentarily or over a period of time). In response to determining that the threshold has been crossed, the control logic can calculate a bolus amount to be delivered. The bolus amount can be based on or be a function of the amount of insulin needed to normalize glucose levels.

SUMMARY

Various alternatives and modifications may be devised by those skilled in the art without departing from the present disclosure. In particular, although the disclosure uses a model-based controller to ultimately determine and deliver an appropriate amount of insulin to a patient, features of the disclosure can apply to other types of control algorithms (e.g., proportional-integral-derivative (PID) control algorithm, a fuzzy logic control algorithm, and the like). Specifically, the various basal rates and the uncorrected meal bolus may be determined by a different type of control algorithm, but the meal bolus correction can be calculated using one or more of the approaches described above.

Accordingly, the present disclosure is intended to embrace all such alternatives, modifications and variances. Additionally, while several embodiments of the present disclosure have been illustrated in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

What is claimed is:

1. A system to control glucose in a patient, the system comprising:
   a medication delivery device configured to deliver insulin to the patient; and
   a controller comprising a processor in communication with the medication delivery device, the controller including control logic operative to:
   calculate a meal bolus,
   calculate a meal bolus correction, wherein:
       the meal bolus correction is calculated by (BG−target)/Si−IOB, where BG is a glucose level, target is a target glucose level, Si is an insulin sensitivity, and IOB is an IOB level, when the glucose level is below a threshold and the IOB level is negative,
       the meal bolus correction is calculated by (BG−target)/Si−IOB, when the glucose level is above the threshold and the IOB level is positive,
       the meal bolus correction is calculated by (BG−target)/Si, when the glucose level is above the threshold and the IOB level is negative, and
       the meal bolus correction is calculated by (BG−target)/Si, when the glucose level is below the threshold and the IOB level is positive, and
   calculate a corrected meal bolus based, at least in part, on the meal bolus and the meal bolus correction, and
   transmit the corrected meal bolus to the medication delivery device,
   wherein in response to receiving the transmitted corrected meal bolus, the medication delivery device is caused to deliver the insulin to the patient.

2. The system of claim 1, wherein the IOB is based, at least in part, on mini-bolus corrections.

3. The system of claim 1, wherein the IOB is based, at least in part, insulin deliveries over a predetermined period of time prior to calculating the meal bolus correction.

4. The system of claim 1, wherein the IOB is calculated by a linear decay model, a curvilinear model, or a two-compartment model.

5. The system of claim 1, further comprising a user interface communicatively coupled to the processor and configured to receive user input.

6. The system of claim 1, wherein the meal bolus is based, at least in part, on a meal carbohydrate content and a carbohydrate ratio.

7. The system of claim 1, further comprising the insulin contained in the medication delivery device.

8. The system of claim 1, further comprising:
   a glucose measurement device in communication with the controller and configured to measure the glucose level.

9. A method comprising:
   using a processor to obtain a meal bolus;
   calculating, by the processor, a meal bolus correction, wherein:
       the meal bolus correction is calculated by (BG−target)/Si−IOB, where BG is a glucose level, target is a target glucose level, Si is an insulin sensitivity, and IOB is an IOB level, when the glucose level is below a threshold and the IOB level is negative,
       the meal bolus correction is calculated by (BG−target)/Si−IOB, when the glucose level is above the threshold and the IOB level is positive,
       the meal bolus correction is calculated by (BG−target)/Si, when the glucose level is above the threshold and the IOB level is negative, and
       the meal bolus correction is calculated by (BG−target)/Si, when the glucose level is below the threshold and the IOB level is positive;
   calculating, by the processor, a corrected meal bolus based, at least in part, on the meal bolus and the meal bolus correction; and
   transmitting the corrected meal bolus to a medication delivery device configured to deliver medication to a patient, wherein in response to receiving the transmitted corrected meal bolus, the medication delivery device is caused to deliver insulin to the patient.

10. A non-transitory computer-readable medium includes instructions that cause a hardware processor to:
   calculate a meal bolus;
   calculate a meal bolus correction, wherein:
       the meal bolus correction is calculated by (BG−target)/Si−IOB, where BG is a glucose level, target is a target glucose level, Si is an insulin sensitivity, and IOB is an IOB level, when the glucose level is below a threshold and the IOB level is negative,
       the meal bolus correction is calculated by (BG−target)/Si−IOB, when the glucose level is above the threshold and the IOB level is positive,
       the meal bolus correction is calculated by (BG−target)/Si, when the glucose level is above the threshold and the IOB level is negative, and
       the meal bolus correction is calculated by (BG−target)/Si, when the glucose level is below the threshold and the IOB level is positive;
   calculate a corrected meal bolus based, at least in part, on the meal bolus and the meal bolus correction; and
   transmit the corrected meal bolus to a medication delivery device configured to deliver medication to a patient, wherein in response to receiving the transmitted corrected meal bolus, the medication delivery device is caused to deliver insulin to the patient.

\* \* \* \* \*